(12) United States Patent
Tropsch et al.

(10) Patent No.: US 7,863,479 B2
(45) Date of Patent: Jan. 4, 2011

(54) ALKYL ETHER SULFATES

(75) Inventors: Juergen Tropsch, Roemerberg (DE); Thomas Zelinski, Neuleiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 244 days.

(21) Appl. No.: 10/588,217

(22) PCT Filed: Feb. 10, 2005

(86) PCT No.: PCT/EP2005/001319

§ 371 (c)(1), (2), (4) Date: Aug. 2, 2006

(87) PCT Pub. No.: WO2005/077893

PCT Pub. Date: Aug. 25, 2005

(65) Prior Publication Data

US 2008/0207939 A1    Aug. 28, 2008

(30) Foreign Application Priority Data

Feb. 12, 2004    (DE) ................. 10 2004 007 152

(51) Int. Cl.
  C07C 309/63    (2006.01)
  A61K 8/02    (2006.01)
  A61K 8/39    (2006.01)
  C11D 1/83    (2006.01)
  C11D 17/00    (2006.01)

(52) U.S. Cl. .............. 562/36; 424/401; 514/578; 510/119; 510/127; 510/128; 510/130; 510/135; 510/276

(58) Field of Classification Search ............... None
See application file for complete search history.

(56) References Cited

U.S. PATENT DOCUMENTS

| | | | |
|---|---|---|---|
| 3,843,706 A | | 10/1974 | Weil et al. |
| 4,726,915 A | * | 2/1988 | Verdicchio .............. 510/469 |
| 4,830,764 A | * | 5/1989 | Wiedemann ............ 435/233 |
| 4,889,945 A | * | 12/1989 | Wiedemann ............ 558/186 |

FOREIGN PATENT DOCUMENTS

| | | |
|---|---|---|
| DE | 44 36 066 | 4/1996 |
| EP | 0 167 337 | 1/1986 |
| EP | 1 354 872 | 10/2003 |
| JP | 6 17088 | 1/1994 |
| JP | 6 17089 | 1/1994 |
| WO | 94 11330 | 5/1994 |
| WO | 95 15408 | 6/1995 |
| WO | 99 65972 | 12/1999 |
| WO | 00 58428 | 10/2000 |

OTHER PUBLICATIONS

Organic Chemistry, 4th Edition, Ralph J. Fessenden and Joan S. Fessenden, Brooks Cole Publishing Company, 1990, p. 96.*
Weil, James K. et al.,"Oxypropylation of Fatty Alcohols, and the Sulfation Products", Journal of American Oil Chemists' Society, vol. 43, pp. 157-160, 1966.
Shinoda, Kozo et al.," Ionic Surfactants Soluble in Hard Water and in Hydrocarbons: Behavior of Organized Surfactant Solutions as a Function of the Hydrophilic-Lipophilic Balance", Journal of Physical Chemistry, vol. 90, No. 7, pp. 1228-1230, 1986.
Weil, James K. et al.,"Synthesis and Surface Active Properties of Long Chain Ether Alcohol Sulfates R(OCH$_2$CHR')$_i$OSO$_3$Na", Chim. Phys. Appl. Prat. Ag. Surface, C. R. Congr. Int. Deterg. 5$^{th}$, vol. 1, pp. 45-51, 1969.
Murata, M. et al.,"New Anionic Surfactants Being Resistant to hard Water: Sodium Alkyl Ether Sulfates Having Oxypropylene Groups", Comun. Journ. Com. Esp. Deterg., 1981. (Abstract Only).
Minana-Perez, Matilde et al.,"Sulubilization of Polar Oils With Extended Surfactants", Colloids Surfaces A : Physicochem. Eng. Aspects, vol. 100, pp. 217-224, 1995.
U.S. Appl. No. 12/783,804, filed May 20, 2010, Seebeck, et al.
U.S. Appl. No. 12/783,726, filed May 20, 2010, Seebeck, et al.

* cited by examiner

*Primary Examiner*—Fiona T Powers
(74) *Attorney, Agent, or Firm*—Oblon, Spivak, McClelland, Maier & Neustadt, L.L.P.

(57) ABSTRACT

The present invention relates to alkyl ether sulfate salts of the general formula I $$RO-(CH_2CH_2O)_x-(CH_2-CHR^1O)_y-(CH_2CH_2O)_zSO_3^-M^+ \quad (I),$$

where
R is an unbranched or branched $C_8$-$C_{18}$-alkyl radical or mixtures of different unbranched or branched $C_8$-$C_{18}$-alkyl radicals,
$R^1$ is an aliphatic radical selected from the group consisting of methyl and ethyl,
$M^+$ is a cation, selected from the group consisting of alkali metals, $NH_4^+$ and $HNR^2_3{}^+$, where $R^2$ is selected from the group consisting of unbranched or branched alkyl radicals, $CH_2CH_2OH$ and $CH_2CH(OH)CH_3$,
x has a mean value of 0-3,
y has a mean value of 1-10,
z has a mean value of 0-30,
and the quotient

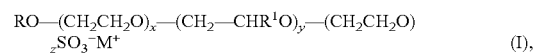

and to their use as anion surfactant component in laundry detergents and cleaning compositions, in chemical engineering applications or in cosmetics formulations.

13 Claims, No Drawings

ALKYL ETHER SULFATES

The present invention relates to alkyl ether sulfate salts from alkoxylated alcohols which are sulfonated, these alkyl ether sulfate salts having, between the alcohol component and the sulfate group, propylene and/or butylene oxide units and if appropriate ethylene oxide units, and also relates to the use of these alkyl ether sulfate salts in laundry detergents and cleaning compositions.

From the prior art, the use of alkyl ether sulfate salts, for example as surfactants, is already known.

EP-A-1354872 relates to a process for preparing salts consisting of amines and sulfuric esters. The sulfuric esters can bear in the side chain on average from 0.1 to 10 oxyalkylene units having from 2 to 4 carbons.

WO 00/58428 discloses a self-thickening heat-activatable cleaning composition which comprises anionic surfactants, for example alkyl benzene sulfates, ethoxylated alkyl ether sulfate salts and propoxylated alkyl ether sulfate salts.

WO 99/65972 relates to an aqueous emulsion comprising at least one resin which contains silicone-containing building blocks and is a reaction product of ammonia or polyfunctional aromatic or aliphatic amine, carboxylic acids or carboxylic anhydrides and nonionic, anionic or amphoteric surfactants. The anionic surfactants here can be ethoxylated and propoxylated derivatives of alkyl sulfate salts having on average from 0.5 to 10 ethylene oxide and/or propylene oxide units.

WO 95/15408 discloses a process for etching aluminum or aluminum alloys in a caustic bath comprising an anionic surfactant of the sulfate or sulfonate type.

JP 06017089 and JP 06017088 relate to a milky cleaning composition having a pearly appearance and good long-term stability and excellent cleaning action comprising an alkyl glycoside, an anionic surfactant and the salt of a sulfuric ester of an alcohol-propylene oxide adduct having a mean molecular weight of from 400 to 4000.

It is an object of the present invention to provide alkyl ether sulfate salts which can advantageously be used as anionic surfactants in laundry detergents and cleaning compositions.

We have found that this object is achieved according to the invention by alkyl ether sulfate salts of the general formula I $$RO-(CH_2CH_2O)_x-(CH_2-CHR^1O)_y-(CH_2CH_2O)_z SO_3^- M^+ \quad (I),$$

where

R is an unbranched or branched $C_8$-$C_{18}$-alkyl radical or mixtures of different unbranched or branched $C_8$-$C_{18}$-alkyl radicals, $R^1$ is methyl, ethyl or mixtures thereof, $M^+$ is a cation, selected from the group consisting of alkali metals, $NH_4^+$ and $HNR^2_3{}^+$, where $R^2$ is selected from the group consisting of unbranched or branched alkyl radicals, $CH_2CH_2OH$ and $CH_2CH(OH)CH_3$, x has a mean value of 0-3, in particular 0, y has a mean value of 1-10, z has a mean value of 0-30, for which the quotient A of the critical micelle concentration cmc $$A = \frac{cmc(RO-(CH_2CH_2O)_z SO_3^- M^+)}{cmc(RO-(CH_2CH_2O)_x-(CH_2-CHR^1O)_y-(CH_2CH_2O)_z SO_3^- M^+)} \text{ is} > 1.$$

Preferably, in the inventive alkyl ether sulfate salts of the general formula I, R, $R^1$, x, y, z and $M^+$ have the following meanings:

R is an unbranched or branched $C_{10}$-$C_{18}$-alkyl radical or mixtures of different unbranched or branched $C_{10}$-$C_{18}$-alkyl radicals, $R^1$ is methyl $M^+$ is a cation selected from the group consisting of alkali metals, $NH_4^+$ and $HNR^2_3{}^+$, where $R^2$ is selected from the group consisting of unbranched or branched alkyl radicals, $CH_2CH_2OH$ and $CH_2CH(OH)CH_3$, x has a mean value of 0-2, in particular 0, y has a mean value of 1-3, z has a mean value of 0-10, and the quotient A is greater than 1.

Particularly preferably, in the inventive alkyl ether sulfate salts of the general formula I, R, $R^1$, x, y and z have the following meanings:

R is an unbranched or branched $C_{10}$-$C_{15}$-alkyl radical or mixtures of different unbranched or branched $C_{10}$-$C_{15}$-alkyl radicals, $R^1$ is methyl, x is 0, y has a mean value of 1-2, z has a mean value of 0-4, and the quotient A is greater than 1.

Very particularly preferably, in the inventive alkyl ether sulfate salts of the general formula I, R, $R^1$, x, y and z have the following meanings:

R is a radical derived from 2-propylheptanol, $iC_{13}$ alcohols or mixtures of 2-propyl alcohol and $iC_{1-3}$ alcohols, $R^1$ is methyl, x is 0, y has a mean value of 2, z has a mean value of 0, 1 or 3, and the quotient A is greater than 1.

The invention relates to a defined selection of the known alkyl ether sulfate salts which correspond to the general formula I and which, for A, give a value which is greater than 1.

The quotient $$A = \frac{cmc(RO-(CH_2CH_2O)_z SO_3^- M^+)}{cmc(RO-(CH_2CH_2O)_x-(CH_2-CHR^1O)_y-(CH_2CH_2O)_z SO_3^- M^+)}$$

describes the ratio of the cmc, that is to say the critical micelle concentration, of alkyl ether sulfate salts which, bound to the long-chain alcohol (RO—), then solely have ethylene oxide units or no alkoxide units, to the cmc of alkyl ether sulfate salts which, between the long-chain alcohol (RO—) and the sulfate group optionally have ethylene oxide and other alkylene oxide units ($CH_2$—$CHR^1O$) different from ethylene oxide.

It has been found that alkyl ether sulfate salts of the general formula I which form a quotient A which is greater than 1 exhibit particularly favorable properties when they are used as anionic surfactant component in laundry detergent and cleaning compositions, in chemical applications, or in cosmetics formulations.

It follows herefrom that inventive alkyl ether sulfate salts of the general formula I, compared with the corresponding alkyl ether sulfate salts which if appropriate solely have ethylene oxide units or no alkoxide units exhibit a lower value for the critical micelle concentration (cmc), from which are value of A results which is greater than 1. This fraction of the alkyl ether sulfate salts can be determined by synthesizing the inventive alkyl ether sulfate salts and synthesizing the corresponding alkyl ether sulfate salts optionally containing solely ethylene oxide units or no alkoxide units and comparing the critical micelle concentration (cmc).

The values of the critical micelle concentration (cmc) in mmol/l are determined via concentration series using the DeNuoy method of surface tension measurement.

The quotient A which describes the ratio between the micelle concentrations of the alkyl ether sulfate salts optionally containing solely ethylene oxide units and the inventive alkyl ether sulfate salts according to the invention has a value of greater than 1 to 100, preferably A has a value of greater than 1 to 50, very particularly preferably, A has a value of greater than 1 to 20.

The quotient A is, in the abovementioned limits, preferably greater than 1.1, particularly preferably greater than 1.2 and very particularly preferably greater than 1.5.

The inventive alkyl ether sulfate salts are distinguished by the fact that they have a critical micelle concentration which is to be compared with the cmc of longer-chain alcohols.

Micelles are aggregates of dissolved molecules that are formed by association. In the narrower sense, those aggregates which form from surfactant molecules in aqueous solutions above a certain temperature and a characteristic concentration are designated micelles. This concentration is designated the critical micelle concentration (cmc). Attainment of the critical micelle concentration may be recognized by an abrupt change in physical properties. When the critical micelle concentration is exceeded, the concentration of molecules in the solution is virtually constant and the excess molecules form micelles.

It is inferred from this that the inventive alkyl ether sulfate salts, owing to their lower critical micelle concentration, form, at a lower concentration in aqueous solution, micelles which are necessary for a good surfactant action. As a result, by means of the inventive alkyl ether sulfate salts, the dosage of surfactants in laundry detergents and cleaning compositions can be reduced.

If the inventive examples 1 to 6 and the corresponding reference examples 1 to 6 are considered, it becomes apparent that the cmc values of the inventive alkyl ether sulfate salts 1 to 6 are lower throughout than in the corresponding reference examples 1 to 6 each of which have only ethylene oxide and no propylene oxide or butylene oxide bound directly to the corresponding alcohol.

The inventive alkyl ether sulfate salts of the general formula I can be prepared by one of the following methods:

The corresponding alcohol alkoxide components can be converted into the inventive alkyl ether sulfate salts of the general formula I by sulfating them in a manner known per se using sulfuric acid or sulfuric acid derivatives to give acid alkyl ether sulfate salts.

Sulfation reactions of alcohols have already been described, for example in U.S. Pat. No. 3,462,525, 3,420,875 or 3,524,864. Details on carrying out this reaction are also given in "Ullmann's Encyclopedia of Industrial Chemistry", 5th edition, Vol. A25 (1994), pages 779-783 and in the literature references given there.

If sulfuric acid itself is used for the esterification, expediently use is made of from 75 to 100% strength by weight, preferably from 85 to 98% strength by weight, acid (termed "concentrated sulfuric acid" or "monohydrate". The esterification can be formed in a solvent or diluent if it is wanted for control of the reaction, for example heat development. Generally, the alcoholic reactant is introduced first and the sulfation reagent is added gradually with continuous mixing. If complete esterification of the alcohol alkoxide component is desired, the sulfation reagent and the alcohol alkoxide component are used in a molar ratio of from 1:1 to 1:1.5, preferably from 1:1 to 1:1.2. Smaller amounts of sulfation reagent can be advantageous if mixtures of alcohol alkoxylates are used. The esterification is usually carried out at temperatures of from 25 to 85° C., preferably in the range from 45 to 75° C.

If appropriate it can be expedient to carry out the esterification in a low-boiling, water-immiscible solvent and diluent at its boiling point, the water being formed in the esterification being distilled off azeotropically.

Instead of sulfuric acid of the concentration stated above, for the sulfation of the inventive alkanol mixtures, use can also be made, for example, of sulfur trioxide, sulfur trioxide complexes, solutions of sulfur trioxide in sulfuric acid ("oleum"), chlorosulfonic acid, sulfuryl chloride or else sulfamic acid. The reaction conditions must then be modified appropriately.

If sulfur trioxide is used as sulfation reagent, the reaction can also be carried out advantageously in a falling-film reactor in countercurrent or cocurrent flow, if appropriate also continuously.

The batches, after the esterification, are neutralized by adding alkali and, if appropriate after removing excess alkali metal sulfate and any solvent present, are worked up.

If chlorosulfonic acid is used as sulfating reagent, the corresponding alcohol alkoxide component is charged into a stirred apparatus under inert conditions. Under vigorous stirring, a corresponding amount of chlorosulfonic acid is added dropwise. The molar ratio between alcohol component and chlorosulfonic acid is from 0.5:1 to 1:0.5, preferably the ratio is from 0.75:1 to 1:0.75. Very particularly preferably, the molar ratio of alcohol alkoxide component to chlorosulfonic acid is 1:1. After the HCl gas is removed, the reaction batch is adjusted to a slightly alkaline pH using sodium hydroxide solution.

The invention also further relates to the use of the inventive alkyl ether sulfate salts as anion surfactant component in laundry detergents and cleaning compositions.

The inventive alkyl ether sulfate salts can be used in laundry detergents and cleaning compositions as sole anion surfactant component, or else in combination with other anion surfactants, together with the customary constituents.

Preferred embodiments of the laundry detergents and cleaning compositions are powder laundry detergents, compact laundry detergents, super compact laundry detergents, laundry detergent extrudates, laundry detergent gels, liquid laundry detergents, liquid laundry detergent pouches, liquid laundry detergent concentrates, hand dishwashing detergents, dishwashing detergents for mechanical dishwashers, scouring cleaners or scouring milk, handwashing pastes or gels, all-purpose cleaners, glass cleaners, window cleaners, floor cleaners, bath cleaners, WC cleaners, kitchen cleaners, slaughterhouse cleaners, car shampoos or metal cleaners.

In particular, the inventive alkyl ether sulfate salts can be used as anion surfactant component in laundry detergents or hand dishwashing detergents.

Laundry detergents and cleaners of this type have been described many times in the prior art. A very good survey of the mode of action and composition of cleaners and laundry detergents may be found, for example, in Ullmann's Encyclopedia of Industrial Chemistry, 5th edition, Vol. A7, (1986), pages 137 ff. The laundry detergents and cleaning compositions comprise a surfactant or a plurality of surfactants from the same or different surfactant groups and generally further aids and additives which are either required for final formulation and/or which serve to adapt the cleaning compositions and laundry detergents to the intended specific purpose of use or the type of application (cleaning by hand or machinery). Constituents which, in addition to the various surfactants, can be used in varying combinations and proportions in many cleaning compositions and laundry detergents are, for example, builders (sequestering agents) and co-builders, pH regulators, such as inorganic or organic acids, inorganic or organic bases and buffer systems, dispersants, thickeners, enzymes, bleaching systems, hydrotropic compounds as solubilizers, for example urea or alcohols, organic solvents, finely divided abrasive components, for example quartz flour or marble flour, chalk, diatomaceous earth, pumice, polishing rouge or emery, foam controllers for stabilizing or vaporizing the foam, skin-protecting agents and anticorrosives, disinfectant compounds or systems, for example those which contain iodine or which release chlorine or hypochlorous acid, for example dichloroisocyanurate salt, perfume dyes and biocides. An important proportion of the cleaning action of the laundry detergents and cleaning compositions described in the prior art is ascribed to the surfactants present therein. Use is made of ionic surfactants, more precisely not only anionic surfactants, for example alcohol sulfates, alkyl ether sulfate salts, alkylbenzenesulfonates, α-olefin sulfonates, sulfosuccinates, but also cationic surfactants, for example $C_8$ to $C_{16}$-dialkyldimethylammonium halides, dialkoxydimethylammonium halides or imidazolinium salts having a long-chain alkyl residue.

The use of amphoteric surfactants, for example of derivatives of secondary or tertiary amines, for example $C_6$-$C_{18}$-alkylbetaines or $C_6$-$C_{15}$-alkylsulfobetaines or amine oxides such as alkyldimethylamine oxides has already been described.

Nonionic surfactants, in particular also alkoxylates and polyglycosides of longer-chain and long-chain alkanols, in particular having from 8 to 20 carbon atoms, and also alkoxylates of alkylamines and alkylamides are used in laundry detergents and cleaning compositions. It is also known, in particular, to use oxo alcohols having from 10 to 13 carbon atoms in the form of their phosphoric or sulfuric esters and also alkoxylates of these oxo alcohols directly or in the form of their phosphoric or sulfuric esters as surfactants in laundry detergents and cleaning compositions.

In the interests of the most economic possible use of substance, higher economic efficiency and lower environmental pollution, the manufacturers of cleaning compositions and laundry detergents strive for a constant improvement in the efficiency of their products and in particular of the surfactants present therein.

We have now found that the above described inventive alkyl ether sulfate salts, as anion surfactant component in cleaning compositions and laundry detergents, exhibit a considerably superior efficiency compared with known compositions.

The present invention thus further relates to the use of the above-described alkyl ether sulfate salts of the general formula I as anion surfactant component in laundry detergents and cleaning compositions. Furthermore, the laundry detergents and cleaning compositions comprise customarily known aids and additives and if appropriate additional surfactants.

The minimum content of the alkyl ether sulfate salts of the general formula I of the total weight of the inventive laundry detergents and cleaning compositions is high enough that significant action of this additive is displayed.

Expediently, the content of the alkyl ether sulfate salts to be used according to the invention is set so that, in interaction with the remaining constituents of the laundry detergent and cleaning composition, an optimum cleaning action results. Generally, a good cleaning action is achieved when the content of the inventive alkyl ether sulfate salts of the formula I in the laundry detergent and cleaning composition, based on the total weight of the composition, is from 0.01 to 40% by weight, preferably from 0.1 to 35% by weight, in particular from 0.1 to 30% by weight.

The compounds of the general formula I can be unitary substances, but they can also be mixtures in which different substances coming under the general formula I are mixed with one another. The components of these mixtures can differ with respect to the meanings of R, $R^1$ and M, and with respect to the values of x, y and z. This means that the analytical values obtained in the elemental analysis of the inventive alkyl ether sulfate salts of the general formula I, for example the C and H values obtained for the oxo alcohol structural group, and in particular the values of the alkoxy group determination in the back-calculation to the structural formula, lead to fractional values for x, y and z. The mean values of x, y and z are the mean values of the degrees of alkoxylation of the compounds present in the mixtures. These values are integral values in samples containing only one compound. Obviously, such mixtures of substances are also inventive compounds coming under the general formula I which have the described advantages compared with the prior art.

Obviously, the compositions of the cleaners are adapted to the different purposes, as is familiar to those skilled in the art from the prior art. For this, all appropriate aids and additives known from the above described prior art can be added to the laundry detergent and cleaning compositions comprising the inventive alkyl ether sulfate salts of the general formula I.

In many cases it is expedient to combine the inventively used alkyl ether sulfate salts of the general formula I with other nonionic surfactants, for example alcohol alkoxylates, alkylamino alkoxylates, alkylamido alkoxylates, alkylpolyglucosides, or with ionic, preferably anionic, surfactants, for example longer-chain or long-chain alcohol sulfate salts different from the inventive alkyl ether sulfate salts, alkylbenzenesulfonate salts, α-olefin sulfonate salts, sulfosuccinate salts, or with amphoteric surfactants, for example alkylamine oxides, or betaines.

Hereinafter, examples of surfactants of differing nature which are suitable for combination are mentioned:

Suitable nonionic surfactants are, for example, alkoxylated unbranched or branched $C_8$- to $C_{22}$-alcohols, such as fatty alcohol alkoxylates or oxo alcohol alkoxylates. The alkoxylation can be carried out with ethylene oxide, propylene oxide and/or butylene oxide. Surfactants which can be used are in this case all alkoxylated alcohols which preferably contain in added form at least two molecules of an abovementioned alkylene oxide. Those which can also be used here are block polymers of ethylene oxide, propylene oxide and/or butylene oxide, or addition products which contain said alkylene oxides in random distribution. Per mole or alcohol, from 2 to 50 mol, preferably from 3 to 20 mol, of at least one alkylene oxide are used. Preferably, the alkylene oxide used is ethylene oxide. The alcohols preferably have from 10 to 18 carbon atoms. Depending on the type of the alkoxylation catalyst, alkoxylates having a broad or narrow alkylene oxide homolog distribution can be obtained.

A further class of suitable nonionic surfactants are alkylphenol alkoxylates such as alkylphenol ethoxylates having $C_6$- to $C_{14}$-alkyl chains and from 5 to 30 mol of alkylene oxide units.

Another class of nonionic surfactants are alkylpolyglucosides having from 6 to 22, preferably from 8 to 18, carbon atoms in the alkyl chain. These compounds usually contain from 1 to 20, preferably from 1 to 5, glucoside units.

Another class of nonionic surfactants are N-alkylglucamides of the general structures

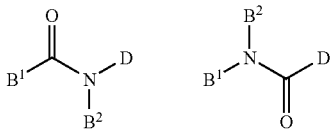

where $B^1$ is a $C_6$- to $C_{22}$-alkyl, $B^2$ is hydrogen or $C_1$- to $C_4$-alkyl and D is a polyhydroxyalkyl radical having from 5 to 12 carbon atoms and at least 3 hydroxyl groups. Preferably, $B^1$ is $C_{10}$- to $C_{18}$-alkyl, $B^2$ is $CH_3$ and D is a $C_5$ or $C_6$ radical. For example, such compounds are obtained by acylating reducing aminated sugars with acid chlorides of $C_{10}$- to $C_{18}$-carboxylic acids.

Other nonionic surfactants which can be used are the end-capped fatty acid amide alkoxylates of the general formula

$$R^3—CO—NH—(CH_2)_n—O-(A^1O)_m—R^4$$

where
$R^3$ is a $C_5$- to $C_{21}$-alkyl or alkenyl radical,
$R^4$ is a $C_1$- to $C_4$-alkyl group,
$A^1$ is $C_2$- to $C_4$-alkylene,
n is the number 2 or 3 and
m has a value of 1-6.

known from WO-A 95/11225.

Examples of such compounds are the reaction products of n-butyl triglycolamine of the formula $H_2N—(CH_2—CH_2—O)_3—C_4H_9$ with methyl dodecanoate or the reaction products of ethyl tetraglycolamine of the formula $H_2N—(CH_2—CH_2—O)_4—C_2H_5$ with a commercially conventional mixture of saturated $C_8$- to $C_{18}$-fatty acid methyl esters.

Compounds which are further suitable as nonionic surfactants are also block copolymers of ethylene oxide, propylene oxide and/or butylene oxide (Pluronic® and Tetronic® brands of BASF), polyhydroxy or polyalkoxy fatty acid derivatives such as polyhydroxy fatty acid amides, N-alkoxy or N-aryloxypolyhydroxy fatty acid amides, fatty acid amide ethoxylates, in particular end-capped compounds, and also fatty acid alkanolamide alkoxylates.

The additional nonionic surfactants are preferably present in the inventive laundry detergents and cleaning compositions in an amount of from 0.01 to 40% by weight, in particular from 0.1 to 35% by weight, especially from 0.5 to 30% by weight.

Individual nonionic surfactants or a combination of different nonionic surfactants can be used. Use can be made of nonionic surfactants from only one class, in particular only alkoxylated $C_8$- to $C_{22}$-alcohols, but use can also be made of surfactant mixtures from different classes.

The inventive alkyl ether sulfate salts can also be used in a mixture with other anionic surfactants. Other anionic surfactants which are suitable are $C_8$- to $C_{24}$-olefin sulfonates and disulfonates, which can be also be mixtures of alkene- and hydroxyalkane-sulfonates or disulfonates, alkyl ester sulfonates, sulfonated polycarboxylic acids, alkylglycerol sulfonates, fatty acid glycerol ester sulfonates, alkylphenolpolyglycol ether sulfates, paraffin sulfonates having from approximately 20 to approximately 50 carbon atoms (based on paraffin or paraffin mixtures produced from natural sources), alkyl phosphates, acyl isethionates, acyl taurates, acyl methyltaurates, alkylsuccinic acids, alkenylsuccinic acids or their half esters or half amides, alkylsulfosuccinic acids or amides thereof, mono- and diesters of sulfosuccinic acids, acyl sarcosinates, sulfated alkylpolyglucosides, alkyl polyglycol carboxylates and hydroxyalkyl sarcosinates.

The anionic surfactants are preferably added to the laundry detergent and cleaning composition in the form of salts. Suitable cations in these salts are alkali metal ions such as sodium, potassium and lithium, and ammonium salts, for example hydroxyethylammonium, di(hydroxyethyl)ammonium and tri(hydroxyethyl)ammonium salts.

The anionic surfactants are present in the inventive cleaning compositions in an amount up to 40% by weight, especially up to 35% by weight, in particular up to 30% by weight. If $C_9$ to $C_{20}$ linear alkylbenzene sulfonates (LAS) are used in conjunction, these are customarily used in an amount of up to 25% by weight, in particular up to 20% by weight.

Individual anionic surfactants or a combination of different ionic surfactants can be used.

In addition, the alkyl ether sulfate salts to be used according to the invention of the general formula I can be combined with cationic surfactants, customarily in an amount of up to 25% by weight, preferably from 0.1 to 15% by weight, for example $C_8$- to $C_{16}$-dialkyldimethylammonium halides, dialkoxydimethylammonium halides or imidazolinium salts having a long-chain alkyl radical; and/or with amphoteric surfactants, customarily in an amount of up to 15% by weight, preferably from 0.1 to 10% by weight, for example derivatives of secondary or tertiary amines, for example $C_6$-$C_{18}$-alkylbetaines or $C_6$-$C_{15}$-alkylsulfobetaines, or amine oxides, such as alkyldimethylamine oxides.

Generally, the alkyl ether sulfate salts to be used according to the invention of the general formula I are combined with builders (sequestering agents), for example polyphosphates, polycarboxylates, phosphonates, complexing agents, for example methylglycinediacetic acid and salts thereof, nitrilotriacetic acid and salts thereof, ethylenediaminetetraacetic acid and salts thereof and if appropriate with co-builders.

Individual builder substances highly suitable for combining with the alkyl ether sulfate salts to be used according to the invention of the general formula I are listed below:

Suitable inorganic builders are, especially, crystalline or amorphous aluminosilicates having ion-exchanging properties, such as in particular zeolites. Various types of zeolites are suitable, in particular zeolites A, X, B, P, MAP and HS in their Na form or in forms in which Na is partially exchanged for other cations, such as Li, K, Ca, Mg or ammonium. Suitable zeolites are described, for example, in U.S. Pat. No. 4,604,224.

Crystalline silicates suitable as builders are, for example, disilicates or sheet silicates, for example $\delta$-$Na_2Si_2O_5$ or $\beta$-$Na_2Si_2O_5$ (SKS 6 and SKS 7). The silicates can be used in the form of their alkali metal salts, alkaline earth metal salts or ammonium salts, preferably as Na, Li and Mg silicates. Amorphous silicates, for example sodium metasilicate which has a polymeric structure, or amorphous disilicate (Britesil® H 20 manufacturer: Akzo) are likewise usable.

Suitable inorganic carbonate-based builder substances are carbonates and hydrogencarbonates. These can be used in the form of their alkali metal, alkaline earth metal or ammonium salts. Preferably, use is made of Na, Li and Mg carbonates or hydrogencarbonates, in particular sodium carbonate and/or sodium hydrogencarbonate.

Customary phosphates used as inorganic builders are alkali metal orthophosphates and/or polyphosphates, for example pentasodium triphosphate.

Said builder components can be used individually or in mixtures with one another.

In a preferred embodiment, the laundry detergents and cleaning compositions which comprise the inventive alkyl ether sulfate salts of the general formula I, additionally to the inorganic builders, comprise from 0.05 to 20% by weight, in particular from 0.1 to 10% by weight, of organic co-builders in the form of low-molecular weight, oligomeric or polymeric carboxylic acids, in particular polycarboxylic acids, or phosphonic acids or salts thereof, in particular Na or K salts.

Low-molecular weight carboxylic acids or phosphonic acids which are suitable as organic co-builders are, for example:

Phosphonic acids, for example 1-hydroxyethane-1,1-diphosphonic acid, amino-tris(methylenephosphonic acid), ethylenediaminetetra(methylenephosphonic acid), hexamethylenediaminetetra(methylenephosphonic acid) and diethylenetriamine-penta(methylenephosphonic acid);

$C_4$- to $C_{20}$-di, -tri and -tetracarboxylic acids, for example succinic acid, propane-tricarboxylic acid, butanetetracarboxylic acid, cyclopentanetetracarboxylic acid and alkyl- and alkenylsuccinic acids having $C_2$- to $C_{16}$-alkyl or alkenyl radicals; $C_4$- to $C_{20}$-hydroxycarboxylic acids, for example malic acid, tartaric acid, gluconic acid, glutaric acid, citric acid, lactobionic acid and sucrose monodi- and tricarboxylic acids; amino-polycarboxylic acids, for example nitrilotriacetic acid; B-alaninediacetic acid, ethylenediaminetetraacetic acid, serinediacetic acid, isoserinediacetic acid, alkylethylenediaminetriacetate, N,N-bis(carboxymethyl)glutamic acid, ethylene-diaminedisuccinic acid and N-(2-hydroxyethyl)iminodiacetic acid, methyl- and ethyl glycinediacetic acid.

Oligomeric or polymeric carboxylic acids which are suitable as organic co-builders are, for example:

Oligomaleic acids, as described, for example, in EP-A 451508 and EP-A 396303; co- and terpolymers of unsaturated $C_4$- to $C_8$-dicarboxylic acids, in which, as comonomers, monoethylenically unsaturated monomers from the group (i) given below can be copolymerized in amounts of up to 95% by weight, from the group (ii) in amounts of up to 60% by weight, and from the group (iii) in amounts of up to 20% by weight.

Suitable unsaturated $C_4$- to $C_8$-dicarboxylic acids are here, for example, maleic acid, fumaric acid, itaconic acid and citraconic acid. Preference is given to maleic acid.

The group (i) comprises monoethylenically unsaturated $C_3$-$C_8$-monocarboxylic acids, for example acrylic acid, methacrylic acid, crotonic acid and vinylacetic acid. Preferably, from the group (i) acrylic acid and methacrylic acid are used.

The group (ii) comprises monoethylenically unsaturated $C_2$- to $C_{22}$-olefins, vinyl alkyl ethers having $C_1$- to $C_8$-alkyl groups, styrene, vinylesters of $C_1$- to $C_8$-carboxylic acids, (meth)acrylamide and vinylpyrrolidone. Preferably, from the group (ii) use is made of $C_2$- to $C_6$-olefins, vinyl alkyl ethers having $C_1$- to $C_4$-alkyl groups, vinyl acetate and vinyl propionate.

If the polymers of group (ii) contain polymerized vinyl ester, these can also be present partially or completely hydrolyzed to vinyl alcohol structural units. Suitable co- and terpolymers are, for example, disclosed by U.S. Pat. No. 3,887,806 and also DE-A 4313909.

The group (iii) comprises (meth)acrylic esters of $C_1$- to $C_8$-alcohols, (meth)acrylonitrile, (meth)acrylamides of $C_1$- to $C_8$-amines, N-vinylformamide and N-vinylimidazole.

Homopolymers of the monoethylenically unsaturated $C_3$-$C_8$-monocarboxylic acids which are suitable as organic co-builders are, for example, acrylic acid, methacrylic acid, crotonic acid and vinylacetic acid, in particular of acrylic acid and methacrylic acid, copolymers of dicarboxylic acids, for example copolymers of maleic acid and acrylic acid in a weight ratio of from 10:90 to 95:5, particularly preferably those in a weight ratio of from 30:70 to 90:10 having molar masses of from 1000 to 150 000; terpolymers of maleic acid, acrylic acid and a vinyl ester of $C_1$-$C_3$-carboxylic acid in a weight ratio of from 10 (maleic acid):90 (acrylic acid+vinyl ester) to 95 (maleic acid):10 (acrylic acid+vinyl ester), in which case the weight ratio of acrylic acid to the vinyl ester can vary in the range from 30:70 to 70:30; copolymers of maleic acid with $C_2$-$C_8$-olefins in a molar ratio of from 40:60 to 80:20, in which case particular preference is given to copolymers of maleic acid with ethylene, propylene, isobutene or diisobutene in a molar ratio of 50:50.

Graft polymers of unsaturated carboxylic acids on low-molecular-weight carbohydrates or hydrogenated carbohydrates, see U.S. Pat. No. 5,227,446, DE-A 4415623 and DE-A 4313909, are likewise suitable as organic co-builders.

Suitable unsaturated carboxylic acids are in this case, for example, maleic acid, fumaric acid, itaconic acid, citraconic acid, acrylic acid, methacrylic acid, crotonic acid and vinylacetic acid, and also mixtures of acrylic acid and maleic acid which are grafted in amounts of from 40 to 95% by weight, based on the component to be grafted.

For the modification, in addition up to 30% by weight, based on the component to be grafted, of further monoethylenically unsaturated monomers can be polymerized. Suitable modified monomers are the abovementioned monomers of the groups (ii) and (iii).

Suitable grafting bases are broken down polysaccharides, for example acidically or enzymatically broken down starches, inulins or cellulose, protein hydrolysates and reduced (hydrogenated or hydrogenating aminated) broken down polysaccharides, for example mannitol, sorbitol, aminosorbitol and N-alkylglucamine, and also polyalkylene glycols having molar masses of up to $M_w$=5000 for example polyethylene glycols, ethylene oxide/propylene oxide or ethylene oxide/butylene oxide or ethylene oxide/propylene oxide/butylene oxide block copolymers and alkoxylated monohydric or polyhydric $C_1$- to $C_{22}$-alcohols (see U.S. Pat. No. 5,756,456).

Polyglyoxylic acids suitable as organic co-builders are, for example, described in EP-B-001004, U.S. Pat. No. 5,399,286, DE-A-4106355 and EP-A-656914. The end groups of the polyglyoxylic acids can have differing structures.

Polyamidocarboxylic acids and modified polyamidocarboxylic acids which are suitable as organic co-builders are disclosed by, for example, EP-A-454126, EP-B-511037, WO-A-94/01486 and EP-A-581452.

As organic co-builders, use is also made in particular of polyaspartic acids or co-condensates of aspartic acid with other amino acids, $C_4$- to $C_{25}$-monocarboxylic or dicarboxylic acids and/or $C_4$- to $C_{25}$-monoamines or diamines. Particularly preferably, use is made of polyaspartic acids prepared in phosphorus-containing acids modified with $C_6$- to $C_{22}$-mono or dicarboxylic acids or modified with $C_6$- to $C_{22}$-mono- or diamines.

Suitable organic co-builders are, furthermore, iminodisuccinic acid, oxydisuccinic acid, aminopolycarboxylates, alkylpolyaminocarboxylates, aminopolyalkylenephosphonates, polyglutamates, hydrophobically modified citric acid, for example agaricic acid, poly-α-hydroxyacrylic acid, N-acylethylenediaminetriacetates such as lauroylethylenediaminetriacetate and alkylamides of ethylenediaminetetraacetic acid such as EDTA tallow amide.

Furthermore, oxidized starches can also be used as organic co-builders.

In a further preferred embodiment, the laundry detergents and cleaning compositions comprising the inventive alkyl ether sulfate salts can additionally, in particular additionally to the inorganic builders, the anionic surfactants and/or the nonionic surfactants, comprise from 0.5 to 20% by weight, in particular from 1 to 10% by weight, of glycine-N,N-diacetic acid derivatives, as are described in WO 97/19159.

Frequently it is also expedient to add, to the laundry detergents and cleaning compositions comprising the inventive alkyl ether sulfate salts, bleaching systems consisting of bleaches, for example perborate, percarbonate and if appropriate bleach activators, for example tetraacetylethylenediamine+bleach stabilizers.

In these cases, the laundry detergents and cleaning compositions comprising the inventive alkyl ether sulfate salts additionally comprise from 0.5 to 30% by weight, in particular from 5 to 27% by weight, especially from 10 to 23% by weight, bleach in the form of percarboxylic acids, for example diperoxododecanedicarboxylic acid, phthalimidopercaproic acid or monoperoxophthalic acid or monoperoxoterephthalic acid, adducts of hydrogen peroxide to inorganic salts, for example sodium perborate monohydrate, sodium perborate tetrahydrate, sodium carbonate perhydrate or sodium phosphate perhydrate, adducts of hydrogen peroxide to organic compounds, for example urea perhydrate, or of inorganic peroxo salts, for example alkali metal persulfates, or alkali metal peroxodisulfates, if appropriate in combination with from 0 to 15% by weight, preferably from 0.1 to 15% by weight, in particular from 0.5 to 8% by weight, of bleach activators.

Suitable bleach activators are:
polyacylated sugars, for example pentaacetylglucose;
acyloxybenzenesulfonic acids and alkali metal and alkaline earth metal salts thereof, for example sodium p-nonanoyloxybenzenesulfonate or sodium p-benzoyloxybenzenesulfonate;
N,N-diacylated and N,N,N',N'-tetraacylated amines, for example N,N,N',N'-tetra-acetylmethylenediamine and N,N,N',N'-tetraacetylethylenediamine (TAED), N,N-diacetylaniline, N,N-diacetyl-p-toluidine or 1,3-diacylated hydantoins such as 1,3-diacetyl-5,5-dimethylhydantoin;
N-alkyl-N-sulfonylcarbonamides, for example N-methyl-N-mesylacetamide or N-methyl-N-mesylbenzamide;
N-acylated cyclic hydrazides, acylated triazoles or urazoles, for example monoacetylmaleic acid hydrazide;
O,N,N-trisubstituted hydroxylamines, for example O-benzoyl-N,N-succinyl-hydroxylamine, O-acetyl-N,N-succinylhydroxylamine or O,N,N-triacetylhydroxylamine;
N,N'-diacylsulfurylamides, for example N,N'-dimethyl-N,N'-diacetylsulfurylamide or N,N'-diethyl-N,N'-dipropionylsulfurylamide;
acylated lactams, for example acetylcaprolactam, octanoylcaprolactam, benzoylcaprolactam or carbonylbiscaprolactam;
anthranil derivatives, for example 2-methylanthranil or 2-phenylanthranil;
triacylcyanurates, for example triacetylcyanurate or tribenzoylcyanurate;
oxime esters and bisoxime esters, for example O-acetylacetone oxime or bisisopropylimino carbonate;
carboxylic anhydrides, for example acetic anhydride, benzoic anhydride, m-chlorobenzoic anhydride or phthalic anhydride;
enol esters, for example isopropenyl acetate;
1,3-diacyl-4,5-diacyloxyimidazolines, for example 1,3-diacetyl-4,5-diacetoxy-imidazoline;
tetraacetylglycoluril and tetrapropionylglycoluril;
diacylated 2,5-diketopiperazines, for example 1,4-diacetyl-2,5-diketopiperazine;
ammonium-substituted nitriles, for example N-methylmorpholiniumacetonitrile methylsulfate;
acylation products of propylenediurea and 2,2-dimethylpropylenediurea, for example tetraacetylpropylenediurea;
α-acyloxypolyacylmalonamides, for example α-acetoxy-N,N'-diacetylmalonamide;
diacyldioxohexahydro-1,3,5-triazines, for example 1,5-diacetyl-2,4-dioxohexa-hydro-1,3,5-triazine;
benz-(4H)1,3-oxazin-4-ones having alkyl radicals, for example methyl, or aromatic radicals, for example phenyl, in the 2 position.

The bleaching system described of bleaches and bleach activators can if appropriate further comprise bleach catalysts. Suitable bleach catalysts are, for example, quaternized imines and sulfonimines which are described, for example, in U.S. Pat. No. 5,360,569 and EP-A 453 003. Particularly active bleach catalysts are manganese complexes which are described, for example, in WO-A 94/21777. Such compounds, when they are used in the cleaning compositions, are incorporated at most in amounts up to 1.5% by weight, in particular up to 0.5% by weight, in the case of very active manganese complexes, in amounts up to 0.1% by weight.

In addition to the described bleach system of bleaches, bleach activators and if appropriate bleach catalysts, it is also possible, for the laundry detergents and cleaning compositions comprising the inventive alkyl ether sulfate salts of the general formula I to use systems having enzymatic peroxide release or photoactivated bleach systems.

For a number of applications it is expedient that the laundry detergents and cleaning compositions comprising the inventive alkyl ether sulfate salts of the general formula I comprise enzymes. Enzymes preferably used in laundry detergents and cleaning compositions are proteases, amylases, lipases and cellulases. Of the enzymes, preferably amounts of from 0.1 to 2.5% by weight, in particular preferably from 0.2 to 1.5% by weight of the formulated enzyme are added. Suitable proteases are, for example, Savinase and Esperase (manufacturer: Novo Nordisk). A suitable lipase is, for example, Lipolase (manufacturer: Novo Nordisk). A suitable cellulase is, for example, Celluzym (manufacturer: Novo Nordisk). The use of peroxidases to activate the bleaching system is also possible. Individual enzymes or a combination of different enzymes can be used. If appropriate, the laundry detergent and cleaning composition comprising the inventive alkyl ether sulfate salts can further comprise enzyme stabilizers, for example calcium propionate, sodium formate or boric acids or salts thereof and/or oxidation inhibitors.

The constituents of laundry detergents and cleaning compositions are known in principle to those skilled in the art. The lists above and below of suitable constituents give only an exemplary excerpt of the known suitable constituents.

The laundry detergents and cleaning compositions comprising the inventive alkyl ether sulfate salts of the general formula I can, in addition to the abovementioned main components, further comprise the following further customary additives in the amounts customary therefor:

Known dispersants, for example naphthalenesulfonic acid condensates or polycarboxylates, pH regulating compounds, for example alkalis (NaOH, KOH, pentasodium metasilicate) or acids (hydrochloric acid, phosphoric acid, amidosulfuric acid, citric acid), buffer systems, for example acetate or phosphate buffer, perfume, dyes, biocides, for example isothiazolinones or 2-bromo-2-nitro-1,3-propanediol, solubilizers/hydrotropes, for example cumenesulfonates, toluenesulfonates, short-chain fatty acids, urea, alcohols or phosphoric alkyl/aryl esters, alkyl/aryl polyglycol phosphoric esters, solvents, for example short-chain alkyloligoglycols such as butyl glycol, butyl diglycol, propylene glycol monomethyl ether, alcohols such as ethanol, isopropanol, aromatic solvents such as toluene, xylene, N-alkylpyrrolidones or alkylene carbonates, thickeners, for example polysaccharides, and/or lightly crosslinked polycarboxylates (for example Carbopol® from Goodrich), finely divided abrasive components, for example quartz flour or marble flour, chalk, diatomaceous earth, pumice or else polishing rouge or emery, foam controllers for stabilizing or vaporizing the foam, skin protectives and anticorrosives, disinfectants compounds or systems, for example those which release chlorine or hypochlorous acid, for example dichloroisocyanurate salt, or which contain iodine.

The laundry detergent and cleaning compositions are usually, but not solely, aqueous and are in the form of microemulsions, emulsions or solutions.

If they should be in solid pulverulent form, use can be made, in addition, of conventional flow-control agents which impart good flowability, meterability and solubility to them and/or which prevent caking and dusts, for example sodium sulfate or magnesium sulfate.

In the case of tableted laundry detergents and cleaning compositions, in addition tableting aids, for example polyethylene glycols having molar masses >1000 g/mol, polymer dispersions and tablet disintegrants, for example cellulose derivatives, crosslinked polyvinylpyrrolidone, crosslinked polyacrylates or combinations of acids and bases, for example citric acid and sodium bicarbonate, to name only a few, are required.

The laundry detergents and cleaning compositions comprising the inventive alkyl ether sulfate salts of the general formula I are surprisingly considerably superior in their cleaning action to comparable laundry detergents and cleaning compositions.

Furthermore, the present invention relates to the use of the inventive alkyl ether sulfate salts of the general formula I in chemical engineering applications.

In particular the present invention relates to the use of the inventive alkyl ether sulfate salts of the general formula I in textile aids, papermaking aids and leather aids, fire-extinguishing foams, pesticide formulations, in emulsion polymerizations, for metal pretreatment, as aids for the ceramics industry, as cooling lubricants or in emulsifying processes.

The present invention further relates to the use of the inventive alkyl ether sulfate salts of the general formula I in cosmetics applications.

In particular the present invention relates to the use of the inventive alkyl ether sulfate salts of the general formula I in shower gels, hair shampoos, bath additives, syndets, lotions, oils/perfume oils, liquid handwashing soaps and emulsifiers or creams.

The present invention further relates to laundry detergents and cleaning compositions or cosmetics formulations comprising alkyl ether sulfate salts of the general formula I, in which case the quotient A as defined above is greater than 1.

EXAMPLES

General Protocol for Sulfating Alcohols/Alcohol Alkoxylates

The alcohol component, the composition of which is described in Table 1, is charged into a stirred apparatus and inert-blanketed with nitrogen. With vigorous stirring, an equimolar amount of chlorosulfonic acid is added dropwise in the course of 4 hours. The temperature is kept below 30° C. during this. Nitrogen is passed under through the viscous solution overnight at room temperature to expel residual HCl. Then, an equimolar amount of 50% strength NaOH is added dropwise to the reaction batch in such a manner that the temperature does not increase above 45° C. The pH may be set to 8-9 using 50% strength NaOH or 50% strength $H_2SO_4$.

| Example | Alcohol | PO (mol) | EO (mol) | Foam as specified by EN 1890, 2 g/l | cmc (mmol/l) | A |
|---|---|---|---|---|---|---|
| 1 | 2-propylheptanol | 2 | 0 | 600 | 1.81 | 13.06 |
| Reference 1 | 2-propylheptanol | 0 | 0 | 0 | 23.64 | |
| 2 | 2-propylheptanol | 2 | 1 | 665 | 1.82 | 11.25 |
| Reference 2 | 2-propylheptanol | 0 | 1 | 580 | 20.48 | |
| 3 | 2-propylheptanol | 2 | 3 | 675 | 1.67 | 4.96 |
| Reference 3 | 2-propylheptanol | 0 | 3 | 620 | 8.29 | |
| 4 | i-$C_{13}$ alcohol | 2 | 0 | 655 | 0.27 | 18.96 |
| Reference 4 | i-$C_{13}$ alcohol | 0 | 0 | 750 | 5.12 | |
| 5 | i-$C_{13}$ alcohol | 2 | 1 | 730 | 0.33 | 3.39 |
| Reference 5 | i-$C_{13}$ alcohol | 0 | 1 | 1050 | 1.12 | |
| 6 | i-$C_{13}$ alcohol | 2 | 3 | 720 | 0.22 | 2.00 |
| Reference 6 | i-$C_{13}$ alcohol | 0 | 3 | 930 | 0.44 | |

PO = propylene oxide,
EO = ethylene oxide,
WAS = wash-active substances,
cmc = critical micelle concentration;
A = cmc (Ref.-Ex. x)/cmc (Ex. x)

The values for the critical micelle concentration (cmc) in mmol/l are determined via concentration series using the DeNuoy method of surface tension measurement.

We claim:

1. An alkyl ether sulfate salt of the formula I

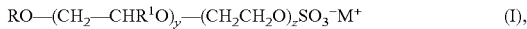

wherein

R is an i-$C_{13}$ group, $R^1$ is methyl, $M^+$ is a cation, selected from the group consisting of alkali metals, $NH_4^+$ and $HNR^2_3{}^+$, where $R^2$ is selected from the group consisting of unbranched or branched alkyl radicals, $CH_2CH_2OH$ and $CH_2CH(OH)CH_3$, y has a mean value of 1-2, z has a mean value of 1-4, for which the quotient A of the critical micelle concentration cmc $$A = \frac{cmc(RO - (CH_2CH_2O)_z SO_3^- M^+)}{cmc(RO - (CH_2 - CHR^1O)_y - (CH_2CH_2O)_z SO_3^- M^+)} \text{ is } > 1.$$

2. At least one of a laundry detergent and a cleaning comprising the alkylether sulfate salt as claimed in claim 1.

3. A composition comprising the alkylether sulfate salt of claim 1, wherein the composition is selected from the group consisting of a powder laundry detergent, a compact laundry detergent, a super compact laundry detergent, a laundry detergent extrudate, a laundry detergent gel, a liquid laundry detergent, a liquid laundry detergent pouch, a liquid laundry detergent concentrate, a hand dishwashing detergent, a dishwashing detergent for mechanical dishwashers, a scouring cleaner, a scouring milk, a handwashing paste, a handwashing gel, an all-purpose cleaner, a glass cleaner, a window cleaner, a floor cleaner, a bathroom cleaner, a WC cleaner, a kitchen cleaner, a slaughterhouse cleaner, a car shampoo and a metal cleaner.

4. A cosmetic composition comprising the alkylether sulfate salt as claimed in claim 1.

5. The cosmetic composition of claim 4, selected from the group consisting of a shower gel, a hair shampoo, a bath additive, a syndet, a lotion, an oil, a perfume oil, a liquid handwashing soap and an emulsifier for a cream.

6. The alkylether sulfate salt of claim 1, wherein R is an i-$C_{13}$ group; $M^+$ is an alkali metal; y has a mean value of 2; and A is >2.

7. The alkylether sulfate salt of claim 1, wherein R is an i-$C_{13}$ group and $M^+$ is an alkali metal.

8. The alkylether sulfate salt of claim 1, wherein A has a value of >1 to 50.

9. The alkylether sulfate salt of claim 1, wherein A is >1.5.

10. The alkylether sulfate salt of claim 1, wherein y has a mean value of 2; z has a mean value of 1 or 3; $M^+$ is an alkali metal; and R is an i-$C_{13}$ group.

11. A method, comprising:
contacting an aqueous solution of the alkyl ether sulfate salt of claim 1 with a laundry textile.

12. A method, comprising:
contacting an aqueous solution of the alkyl ether sulfate salt of claim 1 with a substrate to clean the substrate.

13. A method, comprising:
contacting a composition comprising the alkyl ether sulfate salt of claim 1 with a portion of a human body.

* * * * *